United States Patent
Michal et al.

(10) Patent No.: US 7,470,469 B1
(45) Date of Patent: *Dec. 30, 2008

(54) MEDICAL DEVICE HAVING SURFACE MODIFICATION WITH SUPEROXIDE DISMUTASE MIMIC

(75) Inventors: Eugene T. Michal, San Francisco, CA (US); Murthy Simhambhatla, San Jose, CA (US); Charles D. Claude, San Jose, CA (US)

(73) Assignee: Advanced Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/773,881

(22) Filed: Jul. 5, 2007

Related U.S. Application Data

(60) Continuation of application No. 10/944,319, filed on Sep. 17, 2004, now Pat. No. 7,311,970, which is a division of application No. 10/005,251, filed on Dec. 3, 2001, now Pat. No. 6,793,960, which is a continuation-in-part of application No. 09/827,887, filed on Apr. 6, 2001, now Pat. No. 7,396,582.

(51) Int. Cl.
B05D 3/04 (2006.01)
C07D 225/04 (2006.01)
C07D 225/08 (2006.01)
C08F 2/46 (2006.01)
C08J 7/18 (2006.01)

(52) U.S. Cl. ............ 428/411.1; 424/422; 424/423; 424/424; 540/450; 540/465; 540/466; 540/467; 540/468; 540/469; 540/470; 540/471; 540/474; 623/1.44; 623/1.46; 623/1.49; 623/926; 427/2.1; 427/2.24; 427/2.28; 427/487; 427/488; 427/491; 428/421; 428/422; 428/473.5; 428/423.1; 428/447; 428/500

(58) Field of Classification Search ............ None
See application file for complete search history.

(56) References Cited

U.S. PATENT DOCUMENTS

| | | | |
|---|---|---|---|
| 4,743,327 A | 5/1988 | DeHaan et al. | |
| 4,946,903 A | 8/1990 | Gardella, Jr. et al. | |
| 4,973,394 A | 11/1990 | Ross et al. | |

(Continued)

FOREIGN PATENT DOCUMENTS

WO   WO 91/01210   2/1991

(Continued)

OTHER PUBLICATIONS

Udipi, Kishore, et al., "Modification of Inflammatory Reponse to Implanted Biomedical Materials In Vivo by Surface Bound Superoxide Dismutase Mimics," John Wiley & Sons, Inc., 2000, pp. 549-560.

*Primary Examiner*—Vivian Chen
(74) *Attorney, Agent, or Firm*—Blakely, Sokoloff, Taylor & Zafman LLP

(57) ABSTRACT

A medical device comprising a substrate having a plasma polymerized functionality bonded to at least a portion of the substrate. A superoxide dismutase mimic agent having a complimentary functional group to the plasma polymerized functionality is bonded to the portion of the substrate by bonding to the plasma polymerized functionality. The functionalities can be carboxylate, amine, or sulfate groups and/or polyethylene glycol and can optionally include crosslinking groups.

12 Claims, 8 Drawing Sheets

U.S. PATENT DOCUMENTS

| | | | |
|---|---|---|---|
| 5,061,738 A | 10/1991 | Solomon et al. |
| 5,118,524 A | 6/1992 | Thompson et al. |
| 5,376,400 A | 12/1994 | Goldberg et al. |
| 5,437,900 A | 8/1995 | Kuzowski |
| 5,451,428 A | 9/1995 | Rupp |
| 5,455,040 A | 10/1995 | Marchant |
| 5,610,293 A | 3/1997 | Riley et al. |
| 5,620,649 A | 4/1997 | Trotta |
| 5,723,219 A | 3/1998 | Kolluri et al. |
| 5,752,934 A | 5/1998 | Campbell et al. |
| 5,868,704 A | 2/1999 | Campbell et al. |
| 5,888,591 A | 3/1999 | Gleason et al. |
| 5,891,114 A | 4/1999 | Chien et al. |
| 5,932,299 A | 8/1999 | Katoot |
| 5,962,138 A | 10/1999 | Kolluri et al. |
| 6,048,620 A | 4/2000 | Zhong |
| 6,053,939 A | 4/2000 | Okuda et al. |
| 6,084,093 A | 7/2000 | Riley et al. |
| 6,099,563 A | 8/2000 | Zhong |
| 6,139,525 A | 10/2000 | Davis-Lemessy et al. |
| 6,306,506 B1 | 10/2001 | Timmons et al. |
| 6,505,082 B1 | 1/2003 | Peterfeso et al. |
| 6,541,116 B2 | 4/2003 | Michal et al. |
| 6,730,313 B2 | 5/2004 | Helmus et al. |
| 6,793,960 B1 | 9/2004 | Michal et al. |
| 6,835,387 B2 | 12/2004 | Herrmann |
| 7,311,970 B2 * | 12/2007 | Michal et al. | 428/411.1 |
| 7,396,582 B2 * | 7/2008 | Claude et al. | 428/220 |
| 2002/0146557 A1 | 10/2002 | Claude et al. |
| 2005/0265960 A1 | 12/2005 | Pacetti et al. |
| 2006/0062821 A1 | 3/2006 | Simhambhatla et al. |
| 2006/0121089 A1 | 6/2006 | Michael et al. |

FOREIGN PATENT DOCUMENTS

| | | |
|---|---|---|
| WO | WO 97/42257 | 11/1997 |
| WO | WO 99/32235 | 7/1999 |
| WO | WO 00/32255 | 6/2000 |

* cited by examiner

M40470, R= SCH$_2$CH$_2$NH$_2$

MEDICAL DEVICE HAVING SURFACE MODIFICATION WITH SUPEROXIDE DISMUTASE MIMIC

CROSS REFERENCE TO RELATED APPLICATIONS

This application is a continuation of U.S. patent application Ser. No. 10/944,319 filed on Sep. 17, 2004, now U.S. Pat. No. 7,311,970; which is a divisional application of U.S. patent application Ser. No. 10/005,251 filed on Dec. 3, 2001, now U.S. Pat. No. 6,793,960 issued to Michal, E. et al.; which is a continuation-in-part of U.S. patent application Ser. No. 09/827,887 filed on Apr. 6, 2001, now U.S. Pat. No. 7,396,582, by Claude, C. et al., which is entitled "Medical Device Chemically Modified By Plasma Polymerization."

BACKGROUND OF THE INVENTION

This invention relates to implantable medical devices for therapeutic or diagnostic uses such as endocardial cardiac pacemaker leads and/or cardioverter/defibrillator leads. There are various types of transvenous pacing and cardioversion or defibrillation leads developed for introduction into different chambers of a patient's heart. These implantable leads are usually constructed with an outer biocompatible insulating sheath encasing one or more conductors, one of which is typically attached at its distal end to an exposed tip electrode.

The tip electrode is usually placed in contact with endocardial tissue at the chosen site of the heart chamber by percutaneous introduction and passage through a venous access, often the sub-clavian vein or one of its tributaries, which leads to the heart chamber. As the lead is implanted into the patient, one typical response to this implantation is the fibrotic encapsulation (e.g., protein encapsulations) of the lead. The presence of fibrotic encapsulation can compromise the performance of the lead, especially in more permanent implantation situations. Furthermore, during the removal of the lead, it is typical to require a surgical procedure to remove a portion of the lead. For example, after a portion of a lead is excised from its position, a suspended weight (approximately 5 lbs) is attached to the exposed portion of the lead to allow for an application of a constant force over a period of several hours to extract the lead from the fibrotic encapsulation. Such removal procedure creates discomfort and pain to the patient.

It has been shown in the literature that modification of a plastic (e.g., polyethylene and polyetherurethane) with superoxide dismutase mimic (SODm) results in a significant reduction in fibrotic encapsulation in an implanted foreign device. See "Modification of Inflammatory Response to Implanted Biomedical Materials In Vivo by Surface Bound Superoxide Dismutase Mimics" authored by Kishore Udipi, et. al, Journal of Biomedical Material Research 2000, Sep. 15, 51(4):549-60. The method contemplated by Udipi does not result in a high density grafting of SODm on the surface of the plastic and is dependent on the composition of the substrate.

It would be a significant advantage to provide endocardial cardiac pacemaker leads and/or cardioverter/defibrillator leads or other medical device component having SODm surface treatment with improved bondability and densities, on a variety of substrates including those difficult to modify such as fluoropolymers.

SUMMARY OF THE INVENTION

A medical device coated with superoxide dismutase mimic (SODm) and methods to fabricate the same are described. In one example, the medical device comprises a substrate having a plasma polymerized functionality bonded to at least a portion of the substrate. A superoxide dismutase mimic agent having a complimentary functional group to the plasma polymerized functionality is bonded to the portion of the substrate by bonding to the plasma polymerized functionality.

BRIEF DESCRIPTION OF THE DRAWINGS

The present invention is illustrated by way of example and not limitation in the figures of the accompanying drawings, in which like references indicate similar elements and in which.

DETAILED DESCRIPTION OF THE INVENTION

In the following description, for purposes of explanation, numerous specific details are set forth in order to provide a thorough understanding of the present invention. It will be evident, however, to one skilled in the art that the present invention may be practiced without these specific details. In other instances, specific apparatus structures and methods have not been described so as not to obscure the present invention. The following description and drawings are illustrative of the invention and are not to be construed as limiting the invention.

The present invention is directed to coating implantable medical devices such as endocardial cardiac pacemaker leads and/or cardioverter/defibrillator leads. Exemplary embodiments of the present invention are applicable to the medical devices having components that are designed for being implanted inside a patient's body. These components are often made out of or coated with biocompatible materials such as polymeric materials selected from the group consisting of a fluoropolymer, polytetrafluoroethylene, expanded polytetrafluoroethylene, high density polyethylene, polyimide, polyetherether ketone, polyimide, polyolefin, polyurethane, polycarbonate urethane, siliconized urethane, and silicone rubber. Furthermore, the medical device of the present invention comprises an electrically conductive electrophysiology lead that can be implanted in the patient's heart. Alternatively, the medical device of the present invention comprises a pacemaker lead that can be implanted in the patient's heart. And, the medical device of the present invention comprises an electrical generator and an electrically conductive electrophysiology lead that can be implanted in the patient's heart.

One example of such medical device is a pacemaker lead and/or a cardioverter/defibrillator lead. A pacemaker lead and/or a cardioverter defibrillator lead that the present invention can be applied to has electrical signals generating circuitry for pacing and defibrillating functions. The lead conducts the signals to the appropriate treatment sites in a patient's body. Such a pacemaker lead and/or a cardioverter defibrillator lead are well known in the art. An exemplary pacemaker lead and/or a cardioverter defibrillator lead of the present invention has at least a portion being coated with a SODm coating having functional groups such as amine binding sites or carboxylate binding sites. The portion being coated with SODm is first treated such that it includes a plasma polymerized functionality complimentary to the functional group on the SODm. The exemplary pacemaker lead is coated with a high density SODm layer.

Figure 1:
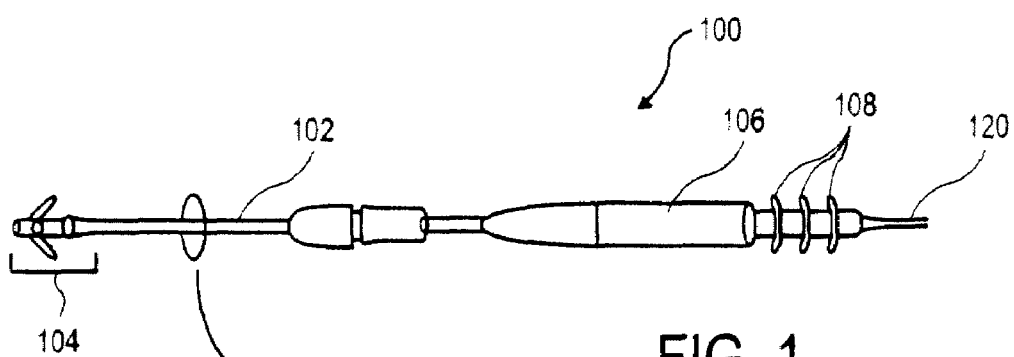
FIG. 1 illustrates an exemplary pacemaker lead of the present invention that can be coated with SODm.

FIG. 1 shows a side view of an exemplary pacemaker lead 100 that the present invention can be applied to. The lead 100 includes an elongated lead body which is covered with an insulation sheath 102. The lead body may be coupled to a tip electrode 104 and a connector assembly 106 having sealing rings 108 which engage connector element or pin 120. Tip electrode 104 is the conductive point for the pacemaker lead and is typically not insulated with insulation sheath 102. Pin 120 may be coupled to an implantable pulse generator (not shown) at the proximal end of the lead body. The connector assembly 106 may be constructed using techniques known in the art and may be fabricated of silicone rubber, polyurethane or other suitable polymer. The connector pin 120 may be fabricated of stainless steel or other conductive material.

Figure 2:
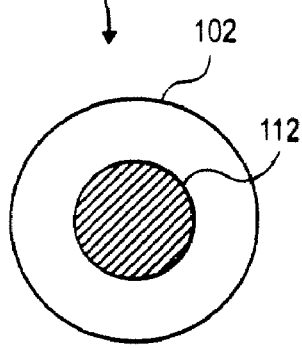
FIG. 2 illustrates a cross-sectional view of the exemplary pacemaker lead of FIG. 1 shown to include a polymeric insulation layer and a conductive element.
Figure 3:
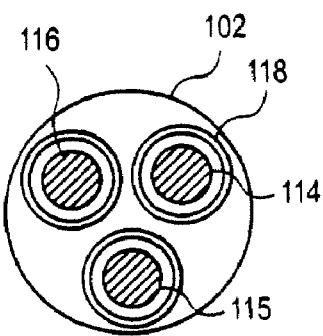
FIG. 3 illustrates a cross-sectional view of the exemplary pacemaker lead of FIG. 1 shown to include a polymeric insulation layer and several conductors.

FIG. 2 illustrates, in a cross-sectional view, that the pacemaker lead in this example also includes a conductive element 112 which is encapsulated by insulation sheath 102 and which is coupled to tip electrode 104. FIG. 3 illustrates that in another embodiment, conductive element 112 may also includes several conductors, (e.g., conductor 114, 115, and 116) each of which may be insulated by a silicone jacket 118. As illustrated, conductive element 112 is coated with insulation sheath 102 which may be fabricated of silicone rubber, polyurethane, fluoropolymers, polytetrafluoroethylene (PTFE), expanded polytetrafluoroethylene (ePTFE), polyolefins such as high density polyethylene (HDPE), and engineering thermoplastic, thermoset polymers such as polyetherether ketone (PEEK), polyimide, urethane, polyurethane, polycarbonate urethane, siliconized urethane, silicone rubber, or any other suitable material. Insulation sheath 102 is generally referred to as polymeric insulation layer 102 throughout this document.

Figure 4:
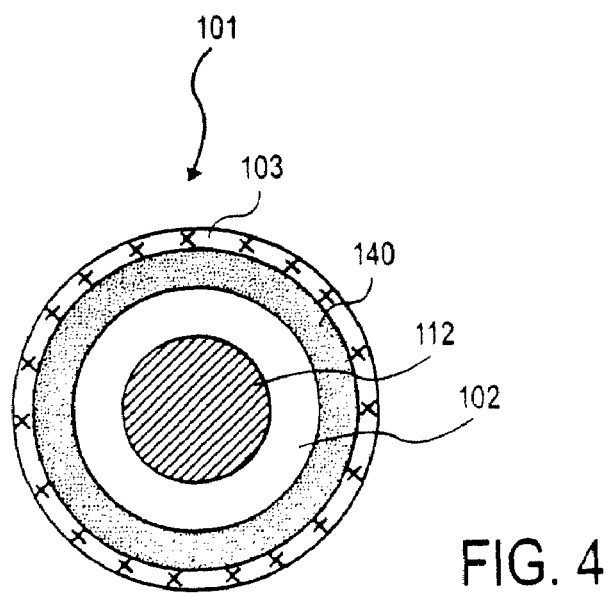
FIG. 4 illustrate a cross-sectional view of the exemplary pacemaker lead of FIG. 1 shown to include a polymeric insulation layer which is treated to include plasma polymerized functionality and coated with a SODm coating.

FIG. 4 illustrates a cross-sectional view of a section 101 of pacemaker lead 100 of the present invention. Section 101 is taken through a portion of the pacemaker lead that will be coated with SODm coatings 103 of the present invention. In a preferred embodiment, section 101 includes portions of pacemaker lead 100 that are implanted inside a patient's body. Section 101, however, does not show electrode tip 104 since that portion is typically the conductive point of pacemaker lead and includes no polymeric insulation layer 102. The electrode tip 104 is electrically conductive and not covered by insulation so that it makes proper electrical contact with the tissue of the patient's body.

In a preferred embodiment, it is to be noted that the electrode tip 104 should remain free of coating to maintain unimpeded electrical conductivity. Thus, no SODm coating will be done to the electrode tip 104.

FIG. 4 further illustrates that pacemaker lead 100 includes conductive element 112 and polymeric insulation layer 102 coated around the conductive element 112. In one example, polymeric insulation layer 102 is a substrate upon which a plasma polymerized functionality layer 140 is formed. As plasma polymerized functionality layer 140 is formed around polymeric insulation layer 112 at least a portion of pacemaker lead 100 is coated with plasma polymerized functionality layer 140. In one example, the entire length of polymeric insulation layer 102 of pacemaker lead 100 is coated with plasma polymerized functionality layer 140. Plasma polymerized functionality layer 140 facilitates the bonding of SODm coating 103 to the surface of the insulation layer with high densities of the SODm molecules on the surface polymeric insulation layer of the lead. In one exemplary embodiment, the SODm coating 103 has a density within the range of 10 $\mu g/cm^2$ to 50 $\mu g/cm^2$. In another embodiment, the SODm coating 103 has a density of 30 $\mu g/cm^2$. For comparison purpose, conventional methods of coating SODm onto a substrate yield an SODm layer having density in the range of 1 $\mu g/cm^2$ to 10 $\mu g/cm^2$. The SODm coating 103 of the present invention thus has a much higher density as compared to conventional methods of forming the SODm layer.

In one example, plasma polymerized functionality layer 140 comprises of functional groups such as carboxylic acid, amine or sulfate. SODm coating 103 includes functionality groups such as amine or carboxylate which is complimentary to the plasma polymerized functionality layer 140 to enhance the bonding of the plasma polymerized functionality layer to the SODm coating 103. In one instance, plasma polymerized functionality layer 140 comprises of carboxylic acid groups and SODm coating 103 comprises of amino groups. These two functionality groups are thus complimentary to each other. In another instance, both the plasma polymerized functionality layer 140 and the SODm coating 103 comprise amine functional groups. A crosslinker is used to bond these two layers together (see FIG. 8).

In one example, only a portion of the lead is coated with plasma polymerized functionality layer 140. The portion that is coated with plasma polymerized functionality layer 140 is the portion that will be coated with SODm coating 103. The remaining portions of plasma polymerized functionality layer 140 of the pacemaker lead thus, may not need to be treated with the plasma polymerized functionality layer 140 and are left for other purposes (e.g., drug delivery) in the use of the pacemaker lead.

In one exemplary embodiment, the surfaces of pacemaker lead 100 is chemically modified by modifying polymeric insulation layer 102. The chemically modified surfaces of pacemaker lead 100 comprise plasma polymerized functionality layer 140 deposited on the surfaces of polymeric insulation layer 102 by plasma polymerization. In a presently preferred embodiment, polymeric insulation layer 102 is chemically modified to create a carboxylate-rich surface from a plasma state derived from an organic carboxylate decomposed in a radio frequency field, which will be denoted as an RF field within the embodiments. However, a variety of suitable functionalities can be plasma polymerized on the surfaces of the pacemaker lead including amine, and sulfate functionalities. In a presently preferred embodiment, the plasma polymerized carboxylate film comprises an acrylate or acrylate-like polymer layer deposited onto the polymeric insulation layer by exposing the polymeric insulation layer to a plasma, which in a presently preferred embodiment is an acrylic acid plasma. One of skill in the art will recognize that some fragmentation of the acrylate typically occurs during plasma polymerization, resulting in an acrylate-like polymer layer of fragmented acrylate. In a presently preferred embodiment, the acrylate is acrylic acid. While discussed below primarily in terms of applying a carboxylate film by plasma polymerization of acrylic acid on the polymeric insulation layer, it should be understood that a variety of functionalities (such as amines) on a variety of substrates may be used.

It will be appreciated that not all portions of a pacemaker lead 100 needs to be chemically modified. The portions that need to be coated with SODm coating 103 are portions to undergo chemical modification. In one exemplary method, the whole pacemaker lead 100 is placed in the reaction chamber for chemical modification. Masking is used to block off the portions that do not need the chemical modification. For instance, a masking agent such as polyvinyl alcohol is coated over the portions (e.g., the distal end of the electrode tip 104 portion) that do not need the chemical modification. This masking can be removed at the end of the process when SODm coating 103 is successfully coated on polymeric insulation layer 102 of pacemaker lead 100.

In a presently preferred embodiment, the polymeric insulation layer is chemically modified to create a carboxylic acid rich surface by exposure to an acrylic acid plasma. In one embodiment, the method comprises introducing the polymeric insulation layer into an argon plasma field to remove organic processing debris from the surface of the polymeric insulation layer before deposition of the plasma polymerized film. The method can be carried out in a plasma reaction chamber 30 illustrated in FIG. 10 (see below). Preferably, polymeric insulation layer 102 is pre-treated in the argon plasma field at about 100 to 250 mTorr, preferably about 150 mTorr, with an applied RF field of about 80 to 250 W, preferably about 100 W, for about 1 to 10 minutes, preferably about 3 minutes. During the pretreatment, argon gas is introduced into the chamber with a flow rate of approximately 230 sccm. After the 3 minute plasma pretreatment, the pressure in the plasma chamber is reduced to less than 1 mTorr.

An acrylic acid plasma is then applied to the polymeric insulation layer to produce a carboxylate rich film on the polymeric insulation layer. The plasma power is formed by an application of a RF field between 20 KHz and 2.45 GHz. In this embodiment the RF field has a frequency of 13.56 MHz. The plasma power together with a flow of acrylic acid creates an acrylic acid plasma having power of about 80 to about 200 W, and preferably about 100 W. The acrylic acid flow rate for the reaction ranges from 0.1 to 0.5 mL/min, and preferably at 0.2 mL/min. The acrylic acid may be mixed with a carrier gas such as carbon dioxide introducing into the chamber with a flow rate of approximately 90 sccm. The pressure for the reaction is maintained at about 150 mTorr. The concentration of the carboxylate is dependent on the decomposition of the acrylic acid in the RF field. The parameters which vary the decomposition of acrylic acid include the plasma power, wherein the carboxylate concentration decreases as the RF power increases. The acrylic acid plasma is applied for about 3 to 10 minutes, preferably about 5 to 10 minutes, depending on the desired thickness of the carboxylate rich film. The thickness of the carboxylate rich film is about 25 to 150 nm, preferably about 50 to about 125 nm. In one embodiment, following exposure to the acrylic acid plasma, the plasma field is purged with argon under no RF power to allow surface free-radicals to recombine before exposure to atmospheric oxygen. For instance, after the reaction time, the RF power is terminated and the pressure in the plasma chamber is reduced to below 1 mTorr. And, upon achieving the low pressure, the plasma chamber is purged with argon gas having a flow rate of approximately 250 sccm while maintaining a pressure of about 230 mTorr with no RP power for 3 minutes. After the 3 minutes, the plasma chamber is vented to atmospheric pressure.

In a presently preferred embodiment, carbon dioxide is included in the acrylic acid plasma to limit the rate of decarboxylation from the surface of the polymeric insulation layer. The composition of polymerized material is dependent on the fragmentation of the acrylic acid. The fragmentation process results in reactive species that polymerize with the substrate surface and species that become nonreactive gaseous products. One such nonreactive gaseous product is a result of the decarboxylation of the acrylic acid with the formation of carbon dioxide. Thus, by adding carbon dioxide to the acrylic acid plasma, the decarboxylation of the organic reactive species in the RF field can be decreased. In a preferred embodiment, the carbon dioxide concentration in the acrylic acid plasma is about 8% to about 10%, preferably about 9%.

The plasma polymerization results in a thin carboxylate film deposited onto the substrate (e.g., polymeric insulation layer 102 of pacemaker lead 100), and will be described as the plasma polymerized functionality within the embodiments. The surface of the substrate has the same polymer composition as the bulk of the substrate, so that the surface and the bulk of the substrate have similar carboxylate concentration following deposition of the plasma polymerized film. The similar carboxylate concentration minimizes the time dependent variation of the surface energy. The structural integrity of the polymeric insulation layer of the lead is minimally or not affected by the plasma polymerization.

In another example, the polymeric insulation layer is chemically modified to create an amine-rich surface by exposure to an allylamine plasma. The same method discussed above can be use. The plasma chamber is fed with allylamine having a flow rate of 0.225 mL/min. A $CO_2$ carrier gas is not required in this example. The plasma power is formed with an RF source of 13.56 MEZ as above. The power is supplied at 30 W and the pressure is maintained at approximately 100 mTorr. All other conditions can be the same as for the creating of the carboxylic acid rich surface discussed above.

The methods to create the plasma polymerized functionality on the pacemaker lead 100 above can be applied to a variety of medical devices made out of a variety of materials. The parameters above may be adjusted to suit different types of materials. For instance, when HDPE, or PTFE is used the power used in the pretreatment step may be lowered to 80-100 W.

Figure 5:
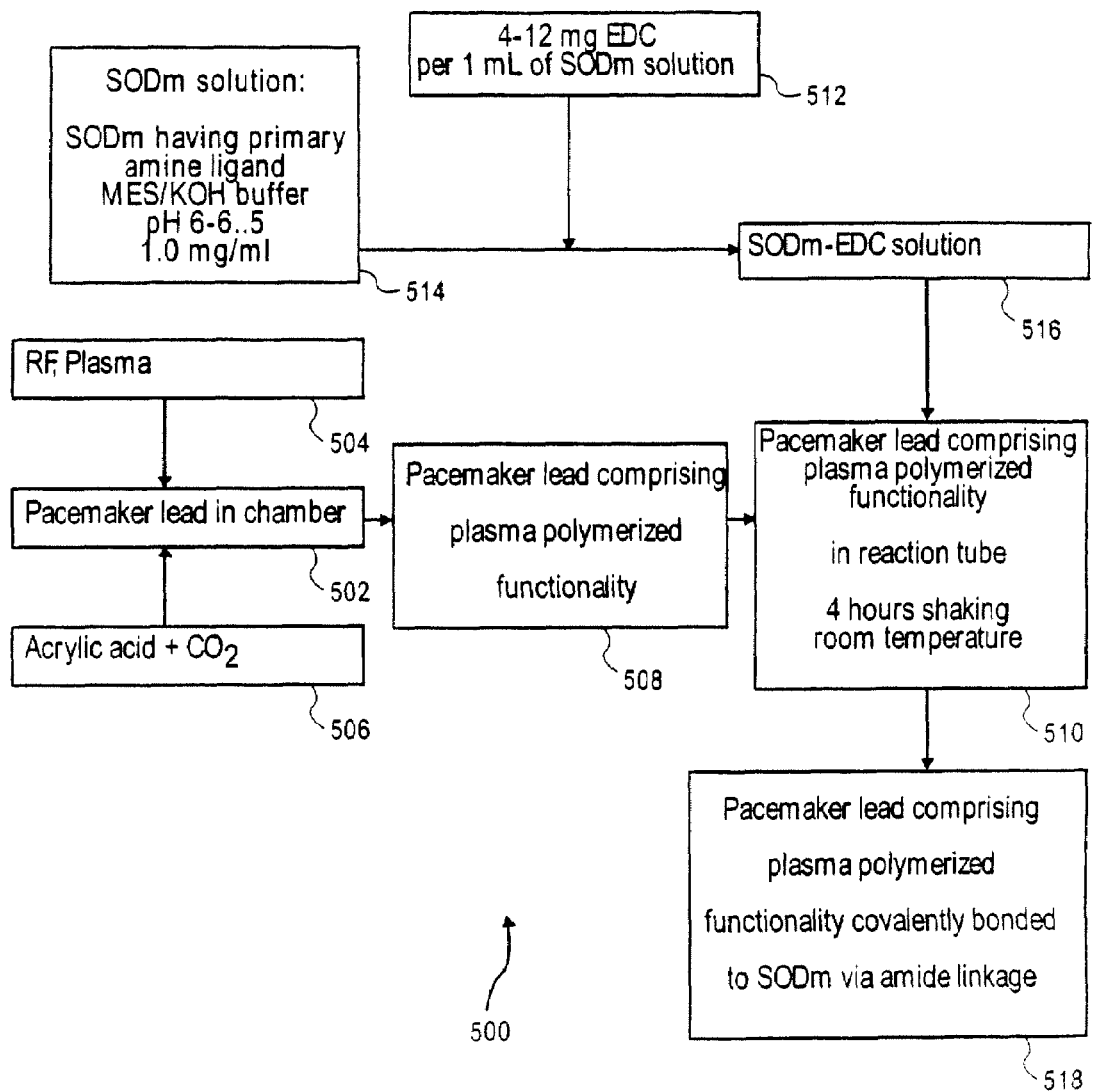
FIG. 5 illustrates an exemplary method of coating a pacemaker lead with SODm.

FIG. 5 illustrates an exemplary method 500 to coat SODm on the surfaces of polymeric insulation layer 102 of pacemaker lead 100 of the present invention. As set forth in steps 502, 504, 506, and 508, pacemaker lead 100 is treated so that it comprises a plasma polymerized functionality including carboxylic functional groups on the surface of polymeric insulation layer 102 of pacemaker lead 100. Steps 502, 504, 506 and 508 are illustrations of the plasma polymerization methods described above. As set forth in step 510, the pacemaker lead 100 comprising plasma polymerized functionality is then placed in a reaction tube (e.g., a glass tube) that allows full-linear covering of the carboxylated pacemaker lead 100 without a 180-degree bend. The carboxylated pacemaker lead 100 is allowed to react with an SODm-EDC solution 516, and in one example, for 4 hours with agitating or shaking at room temperature.

Figure 11:
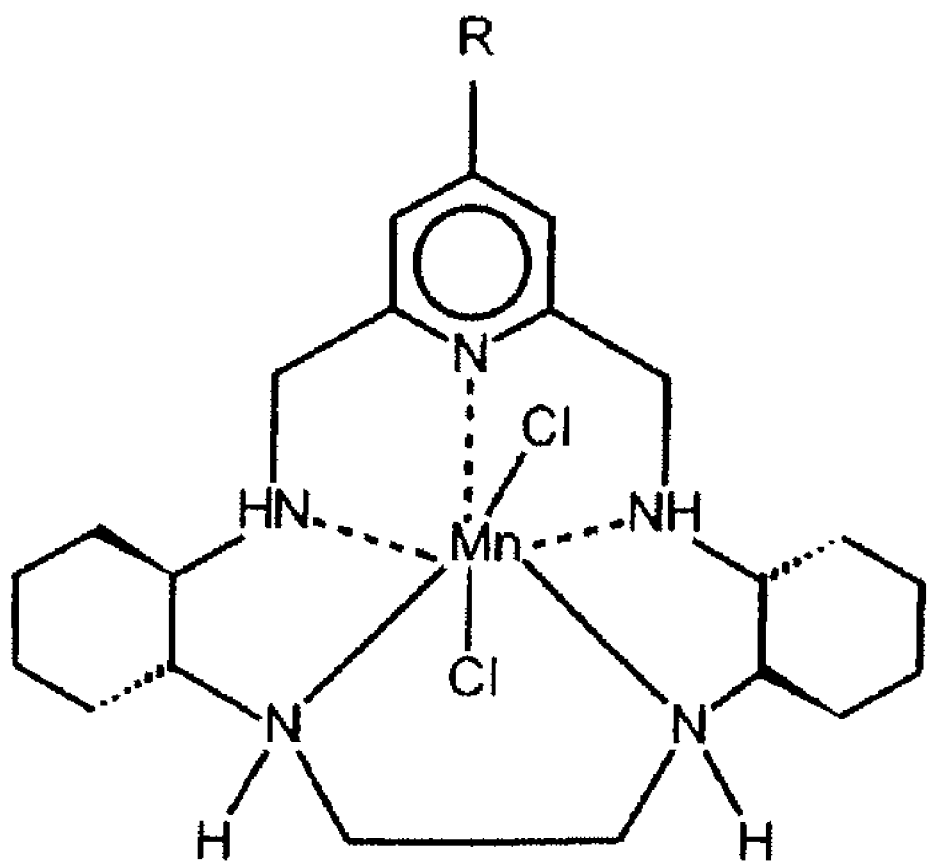
FIG. 11 is the chemical formula for M-40470.

As mentioned, SODm stands for superoxide dismutase mimics, which are low molecular weight molecules that catalyze the conversion of superoxide into oxygen and hydrogen peroxide. In one example, the SODm has a molecular weight ranging from 500 to 600 Da. Examples of SODm include the macrocyclic ligands taught by Riley et al. in U.S. Pat. No. 6,084,093 and U.S. Pat. No. 5,610,293. These patents are hereby incorporated by reference. The SODm including the macrocyclic ligands are related to manganese (II) or manganese (III) complexes of nitrogen-containing fifteen-membered macrocyclic ligands. For example, SODm, also known as M-40470 (see FIG. 11), has the generic chemical name of [manganese (II) dichloro[24-[2-aminoethylthio-](4R,9R,14R, 19R)-3,10,13,20,26-pentaazatetracyclo[20.3.10$^4$,9.0$^{14,19}$]hexacosa-1(26),22(23),24-triene]] with the formula $C_{23}H_{40}N_6Cl_2SMn$. Any variation of the formula above as taught by the Riley patents and any variation of the SODm from ActivBiotics can also be used in accordance with the present invention, provided some functional ligand is available on the molecule for coupling to a surface containing a functional reactive group. Examples of functional reactive groups on a surface for coupling are primary amine, carboxyl, or sulfate. It is to be understood that the above examples are not to be interpreted as limiting.

EDC stands for (1-ethyl-3-[3-dimethylaminopropyl]carbodiimide hydrochloride) which can be obtained from Pierce, Rockford, Ill. In one example, the SODm solution shown at step 514 is prepared by mixing SODm (e.g., M-40470 SODm) having a primary amine ligand in a buffer such as MES/KOH (pH 6-6.5). The SODm solution 514 has a concentration between 0.1 mg/mL to 1.0 mg/mL. The SODm-EDC solution 516 is then created by dissolving EDC from step 512 into SODm solution 514 at 4-12 mg of EDC per 1 mL of SODm solution.

The reaction yields a 0-length amide linkage between the carboxyl surface (the plasma polymerized functionality) on polymerized insulation layer 102 and the SODm amine creating a covalent bonding between the polymeric insulation layer 102 of pacemaker lead 100 and the SODm. The final product is pacemaker lead 100 comprising insulation layer 102 that further comprises plasma polymerized functionality which is covalently bonded to a SODm having amine functional groups via amide linkages as illustrated in box 518. The SODm bonded to the pacemaker lead 100 retains the function of converting superoxide into oxygen and hydrogen peroxide. The presence of the SODm on the pacemaker lead 100 thus significantly reduces fibrotic encapsulation on the pacemaker lead 100.

Figure 6:
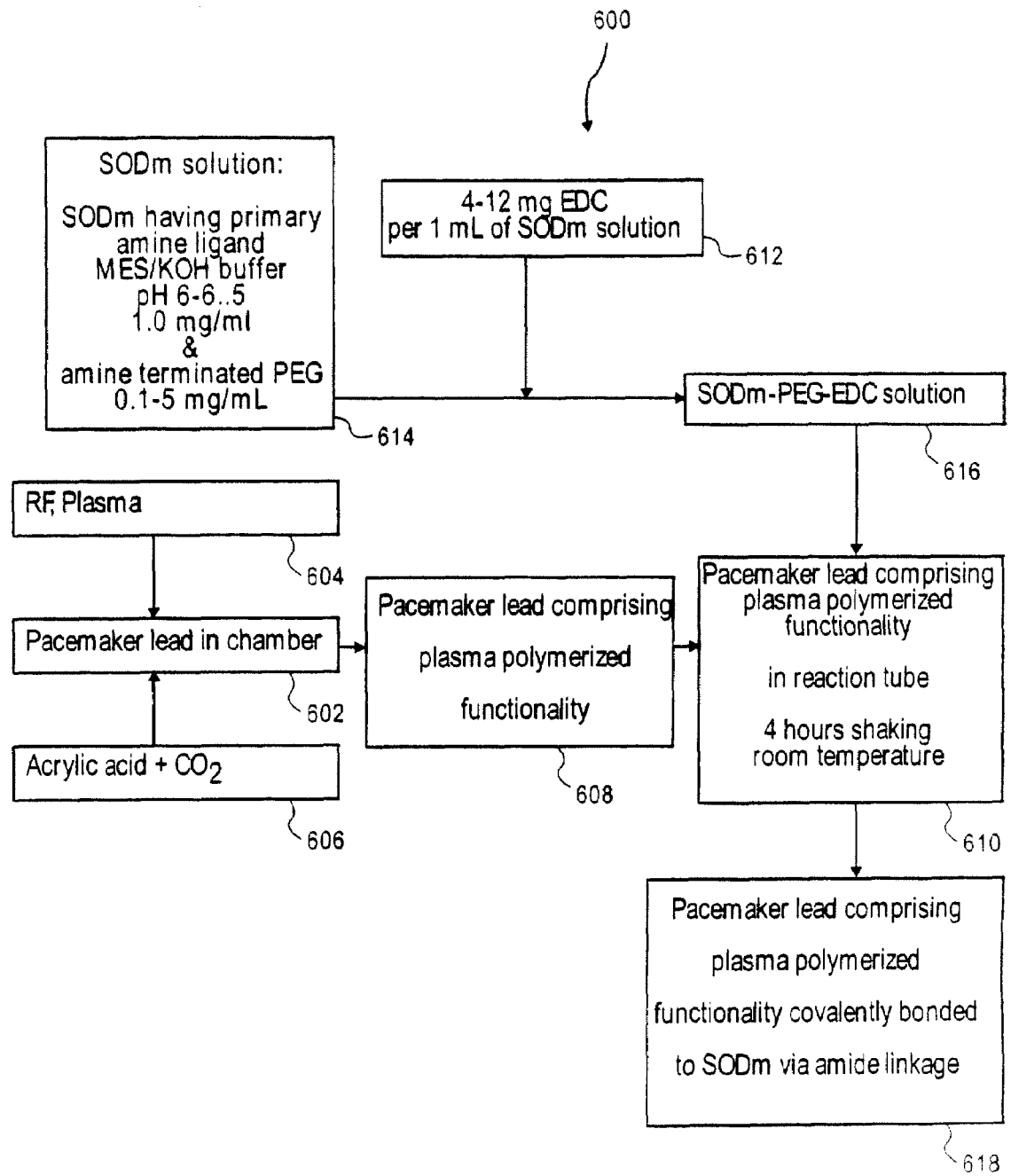
FIG. 6 illustrates another exemplary method of coating a pacemaker lead with SODm.

FIG. 6 illustrates another exemplary method 600 to coat SODm on the surfaces of polymeric insulation layer 102 of pacemaker lead 100 of the present invention. As set forth in steps 602, 604, 606, and 608, pacemaker lead 100 is treated so that it comprises a plasma polymerized functionality including carboxylic functional groups on the surface of polymeric insulation layer 102 of pacemaker lead 100. Steps 602, 604, 606 and 608 are illustrations of the plasma polymerization method described above. As set forth in step 610, pacemaker lead 100 comprising plasma polymerized functionality is then placed in a reaction tube (e.g., a glass tube) that allows full-linear covering of the carboxylated pacemaker lead 100 without a 180-degree bend. The plasma polymerized functionality on pacemaker lead 100 is allowed to react with an SODm-EDC solution 616, and in one example, for 4 hours with agitating or shaking at room temperature.

In one example, the SODm solution shown at step 614 is prepared by mixing SODm (e.g., M-40470 SODm) having a primary amine ligand in a buffer such as MES/KOH (pH 6-6.5). The SODm 614 solution has a concentration between 0.1 mg/mL to 1.0 mg/mL. The SODm solution at step 614 may further include an amine terminated agent such as amine terminated polyethylene glycol (e.g., PEG, from Shearwater 2V3F0F01). The PEG concentration in the SODm solution ranges form 0.1 mg/mL to 5 mg/mL. The SODm-PEG-EDC solution 616 is then created by dissolving EDC from step 612 into SODm solution 614 at a concentration between 4-12 mg of EDC per 1 mL of SODm solution.

The reaction yields a 0-length amide linkage between the carboxyl surface (the plasma polymerized functionality) on polymerized insulation layer 102 and the SODm amine creating a covalent bonding between the polymeric insulation layer 102 of pacemaker lead 100 and the SODm. The final product is pacemaker lead 100 comprising insulation layer 102 that further comprises plasma polymerized functionality which is covalently bonded to a SODm via having amine functional groups amide linkages as illustrated in box 618. The SODm bonded to the pacemaker lead 100 retains the function of converting superoxide into oxygen and hydrogen peroxide. The presence of the SODm on the pacemaker lead 100 thus significantly reduces fibrotic encapsulation on the pacemaker lead 100.

Figure 7:
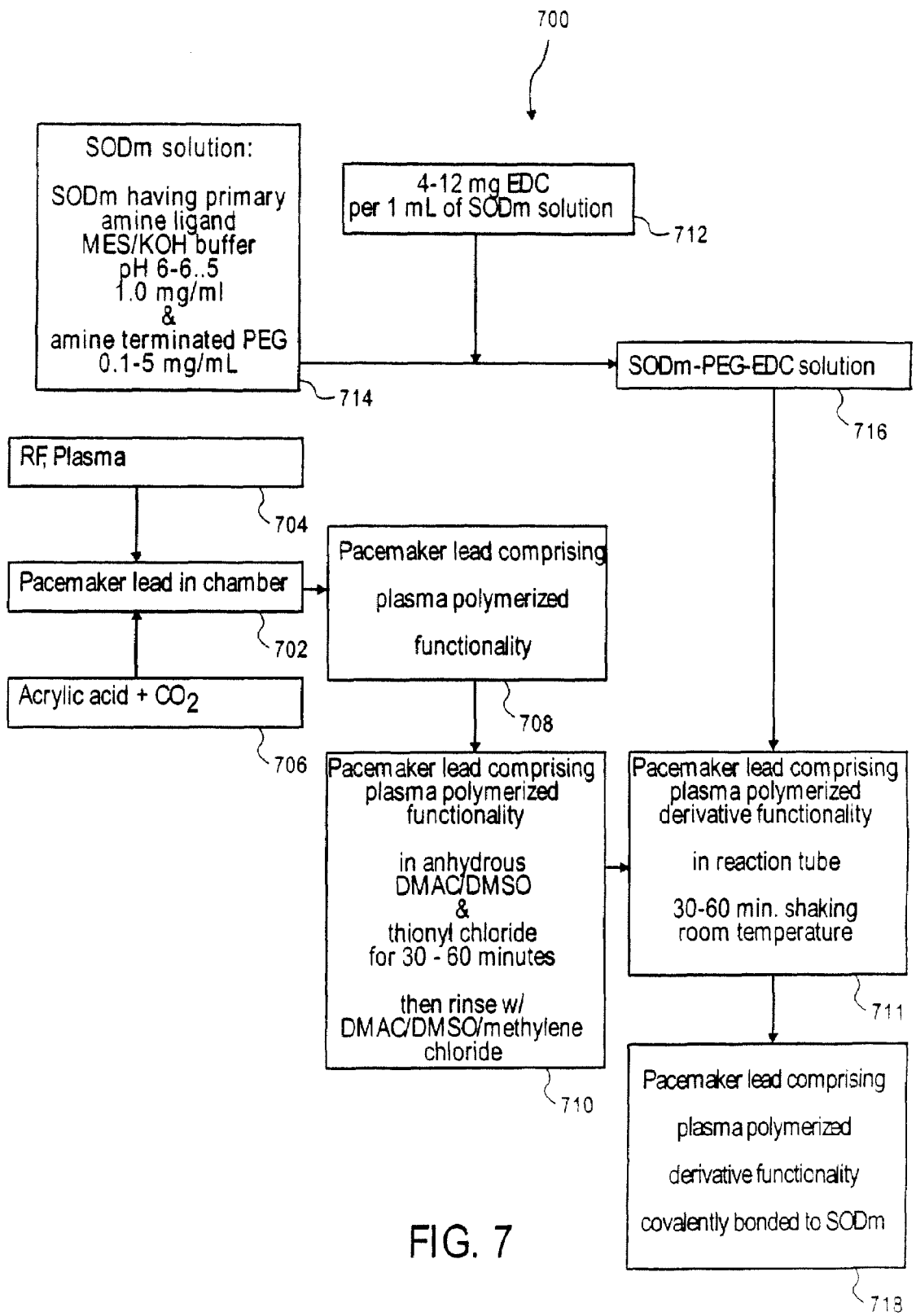
FIG. 7 illustrates yet another exemplary method of coating a pacemaker lead with SODm.

FIG. 7 illustrates yet another exemplary method 700 to coat SODm on the surfaces of polymeric insulation layer 102 of pacemaker lead 100 of the present invention. As set forth in steps 702, 704, 706, and 708, pacemaker lead 100 is treated so that it comprises a plasma polymerized functionality including carboxylic functional groups on the surface of polymeric insulation layer 102 of pacemaker lead 100. Steps 702, 704, 706 and 708 are illustrations of the plasma polymerization method described above.

In this exemplary method, pacemaker lead 100 comprising plasma polymerized functionality is further treated such that the carboxylate functional group on insulation layer 102 is further derivatized with an acid chloride such as thionyl chloride. In one example, step 710 sets forth that pacemaker lead 100 comprising plasma polymerized functionality is dipped in a dipolar aprotic or anhydrous solvent such as N,N-Dimethyl acetamide (DMAC), dimethyl sulfoxide (DMSO), or acetone which includes thionyl chloride at 1% to 10% (w/v) for 30 to 60 minutes. The pacemaker lead 100 is then removed and rinsed with DMAC, DMSO, acetone, or methylene chloride. The pacemaker lead 100 comprising plasma polymerized functionality now includes derivatives that are acid chlorides.

As set forth in step 711, pacemaker lead 100 comprising plasma polymerized functionality and acid chloride derivatives is then placed in a reaction tube (e.g., a glass tube) that allows full-linear covering of the carboxylated pacemaker lead 100 without a 180-degree bend. The pacemaker lead is allowed to react with SODm-PEG-EDC solution 716 for 30 to 60 minutes at room temperature with agitating or shaking.

SODm-PEG-EDC solution 716 is made by mixing EDC and SODm and polyethylene glycol (PEG) together. In one example, the SODm solution shown at step 714 is prepared by mixing SODm (e.g., M-40470 SODm) having a primary amine ligand in a buffer such as MES/KOH (pH 6-6.5). The SODm solution has a concentration between 0.1 mg/mL to 1.0 mg/mL. The SODm solution at step 674 further includes PEG which is an amine terminated agent that can be obtained from Shearwater (catalog #2V3F0F01). The PEG concentration in the SODm solution ranges from 0.1 mg/mL to 5 mg/mL. The SODm-PEG-EDC solution 716 is then finally created by dissolving EDC from step 712 into SODm solution 714 at a concentration between 4-12 mg of EDC per 1 mL of SODm solution.

Alternatively, PEG is not added to the SODm solution 714, this SODm solution is thus similar to solution 514 described in FIG. 5. The SODm-EDC solution 716 is also made similar to the SODm-EDC solution 516 above.

The reaction yields a O-length amide linkage between the carboxyl surface (the plasma polymerized functionality) on polymerized insulation layer 102 and the SODm amine creating a covalent bonding between the polymeric insulation layer 102 of pacemaker lead 100 and the SODm. The final product is pacemaker lead 100 comprising polymeric insulation layer 102 that further comprises plasma polymerized functionality derivatives which is covalently bonded to SODm having amine functional groups via amide linkages as illustrated in box 718. The SODm bonded to the pacemaker lead 100 retains the function of converting superoxide into oxygen and hydrogen peroxide. The presence of the SODm on the pacemaker lead 100 thus significantly reduces fibrotic encapsulation on the pacemaker lead 100.

Figure 8:
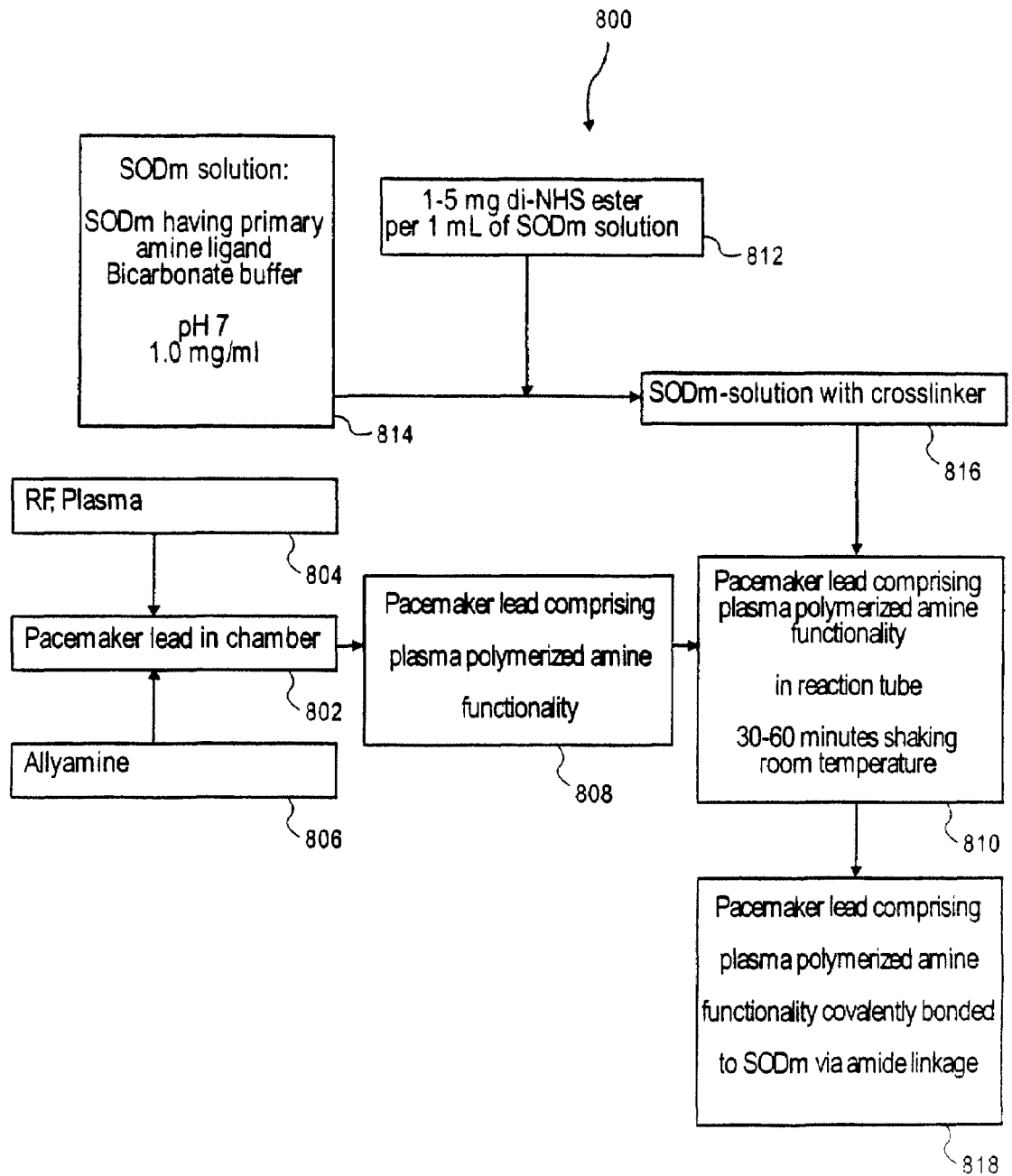
FIG. 8 illustrates further yet another exemplary method of coating a pacemaker lead with SODm.

FIG. 8 illustrates another exemplary method 800 to coat SODm on the surfaces of polymeric insulation layer 102 of pacemaker lead 100 of the present invention. As set forth in steps 802, 804, 806, and 808, pacemaker lead 100 is treated so that it comprises a plasma polymerized functionality including amine functional groups on the surface of polymeric insulation layer 102 of pacemaker lead 100. Steps 802, 804, 806 and 808 are illustrations of the plasma polymerization method described above. As set forth in step 810, pacemaker lead 100 comprising plasma polymerized amine functionality is then placed in a reaction tube (e.g., a glass tube) that allows full-linear covering of the aminated pacemaker lead 100 without a 180-degree bend. The plasma polymerized amine functionality on pacemaker lead 100 is allowed to react with a SODm solution 816 having a crosslinker. In one example, agitating or shaking at room temperature for 30 to 60 minutes is required.

In one example, the SODm solution 816 having the crosslinker is prepared as followed. First, the SODm solution shown at step 814 is prepared by mixing SODm (e.g., M-40470 SODm) having a primary amine ligand in a buffer such as MES/KOH (pH 5.5-6). The SODm solution 814 has a concentration between 0.1 mg/mL to 1.0 mg/mL. In another example, the MES/KOH buffer is replaced with bicarbonate buffer at pH 7.0. Then, the SODm solution 816 having the crosslinker is created by mixing a water soluble crosslinker such as homobifunctional N-hydroxysuccinimide ester (di-NHS ester) from step 812 into SODm solution 814 at a concentration between 1-15 mg di-NHS ester per 1 mL of SODm solution 814. An exemplary di-NHS ester crosslinker includes disulfosuccinimidyl suberate, disuccinimidyl suberate, and bis(sulfosuccinimidyl)suberate made by Pierce.

The reaction yields 2 amide linkages between the amine functional groups (the plasma polymerized functionality) on polymerized insulation layer 102 and the SODm amine creating a covalent bonding between the polymeric insulation layer 102 of pacemaker lead 100 and the SODm. The final product is pacemaker lead 100 comprising insulation layer 102 that further comprises plasma polymerized functionality which is covalently bonded to SODm having amine functionality via amide linkages as illustrated in box 818. The SODm bonded to the pacemaker lead 100 retains the function of converting superoxide into oxygen and hydrogen peroxide. The presence of the SODm on the pacemaker lead 100 thus significantly reduces fibrotic encapsulation on the pacemaker lead 100.

Figure 9:
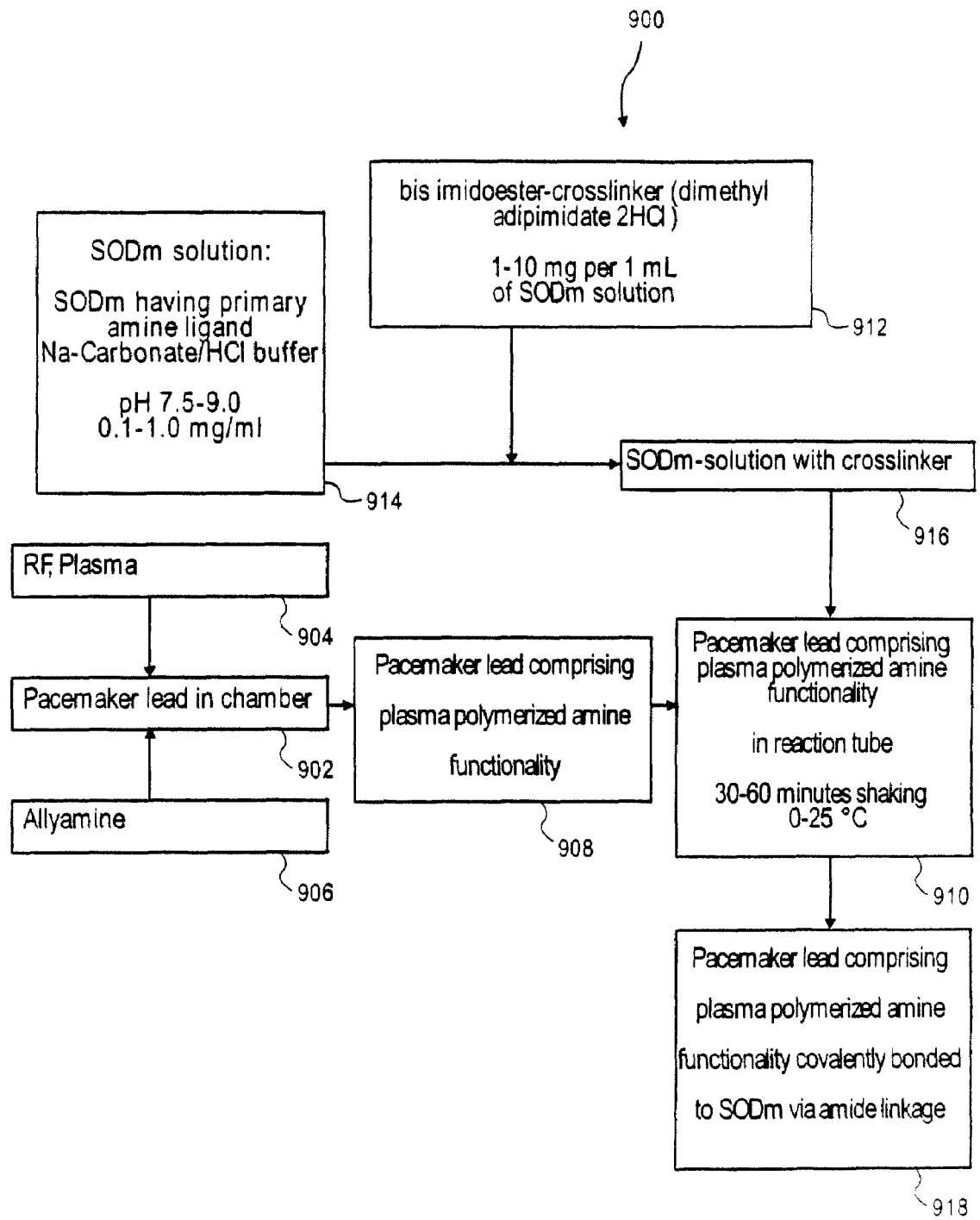
FIG. 9 illustrates another exemplary method of coating a pacemaker lead with SODm.

FIG. 9 illustrates another exemplary method 900 to coat SODm on the surfaces of polymeric insulation layer 102 of pacemaker lead 100 of the present invention. This method is similar to method 800 described above. As set forth in steps 902, 904, 906, and 908, pacemaker lead 100 is treated so that it comprises a plasma polymerized functionality including amine functional groups on the surface of polymeric insulation layer 102 of pacemaker lead 100. Steps 902, 904, 906 and 908 are illustrations of the plasma polymerization method described above. As set forth in step 910, pacemaker lead 100 comprising plasma polymerized amine functionality is then placed in a reaction tube (e.g., a glass tube) that allows full-linear covering of the aminated pacemaker lead 100 without a 180-degree bend. The plasma polymerized amine functionality on pacemaker lead 100 is allowed to react with an SODm solution 916 having a crosslinker. In one example, agitating or shaking at room temperature for 30 to 60 minutes is required.

In one example, the SODm solution 916 having the crosslinker is prepared as followed. First, the SODm solution shown at step 914 is prepared by mixing SODm (e.g., M-40470 SODm) having a primary amine ligand in a high pH buffer such as sodium carbonate/HCl buffer at pH 7.5 to 9.0 and 0.1 mM. The concentration of SODm in the buffer is approximately 0.1 to 1 mg/mL. Then, the SODm solution 916 having the crosslinker is created by dissolving a bis imidoester crosslinker from step 912 into SODm solution 914 at a concentration between 1 to 10 mg of his imidoester crosslinker per 1 mL of SODm solution 914. An exemplary bis imidoester crosslinkers include dimethyl pimelimidate, dimethyl suberimidate, dimethyl adipimidate, and dimethyl 3,3-dithiobispropionimid ate made by Pierce.

The reaction yields 2 imidoamide linkages with a C4 spacer (for dimethyladipimidate) between the amine surface (the plasma polymerized functionality) on the plasma polymerized insulation layer 102 and the SODm amine creating covalent bonding between the polymeric insulation layer 102 of pacemaker lead 100 and the SODm. The final product is pacemaker lead 100 comprising insulation layer 102 that further comprises plasma polymerized functionality which is covalently bonded to SODm having amine functional groups via amide linkages as illustrated in box 918. The SODm bonded to the pacemaker lead 100 retains the function of converting superoxide into oxygen and hydrogen peroxide. The presence of the SODm on the pacemaker lead 100 thus significantly reduces fibrotic encapsulation on the pacemaker lead 100.

The above-described methods can be performed by any suitable apparatus known to one of ordinary skill in the art. One example of such an apparatus is a plasma reaction chamber 30 illustrated in FIG. 10. Chamber 30 can be cylindrical in shape and can be fabricated from any number of suitable materials, such as glass and aluminum. By way of example, chamber 30 can be from about 4 inches (10.16 cm) to about 15 inches (38.1 cm) in diameter and from about 5 inches (12.7 cm) to about 18 inches (45.72 cm) in height.

A mandrel 32 holds a single medical device 34 (e.g., pacemaker lead 100) or multiple medical devices 34 in position relative to the interior wall of chamber 30. Medical device 34 can be oriented at any position within chamber 30 as required to achieve a desired implantations or deposition. One end of mandrel 32 can be coupled to an electrode 36.

Electrode 36 can be made from any suitable electrically conductive material including, but not limited to, steel, copper, chromium, nickel, tungsten, iron, and similar materials. A first power source 38, electrically coupled to electrode 36 via electrical feedthrough port 40, can apply a voltage to electrode 36. In one example, power source 38 is an AC voltage source.

In one embodiment, an insulator 42, formed of a non-electrically conductive material, including materials such as rubber, ceramic, or plastic is provided. Insulator 42 can include a connector 44, which can be either electrically coupled to first power source 38 or an independent second power source 48 for applying a voltage to a cage 50. In one example, a second power source 48 is a DC voltage source.

Cage 50 can be positioned within chamber 30 in symmetrical conformity about medical device 34 so as to protect and reduce dielectric breakdown to medical device 34 due to arcing in the plasma field from all directions. Cage 50 can be manufactured from a conductive material such as carbon, or alternatively, can be made of a base material that is coated with carbon. Alternatively, cage 50 can be made out of other conductive materials such as metals, stainless steel, or titanium. Cage 50 can be cylindrically shaped. Cage 50 can be perforated. By way of example, case 50 can be a perforated cylinder measuring approximately 0.5 inches (1.27 cm) to 3.0 inches (7.62 cm) in diameter, approximately 2 inches (5.08 cm) to 12 inches (30.48 cm) in height, and approximately 1/32 of an inch (0.08 cm) thick. The diameter of the perforations can be from about 0.125 inches (0.318 cm) to about 0.25 inches (0.635 cm). The percentage of the grid occupied by perforation, as opposed to conductive material, can be from about 40% to about 80% of the total surface area.

Gas ports 52 can be positioned on top of chamber 30, while aspiration ports 54 can be positioned at or near the base of chamber 30. Gas ports 52 are used to flux a gaseous medium in liquid or vapor form into chamber 30, where it is converted into ionized plasma. Aspiration ports 54 are used after processing is complete, or when a new gas is desired, purge chamber 30.

Figure 10:
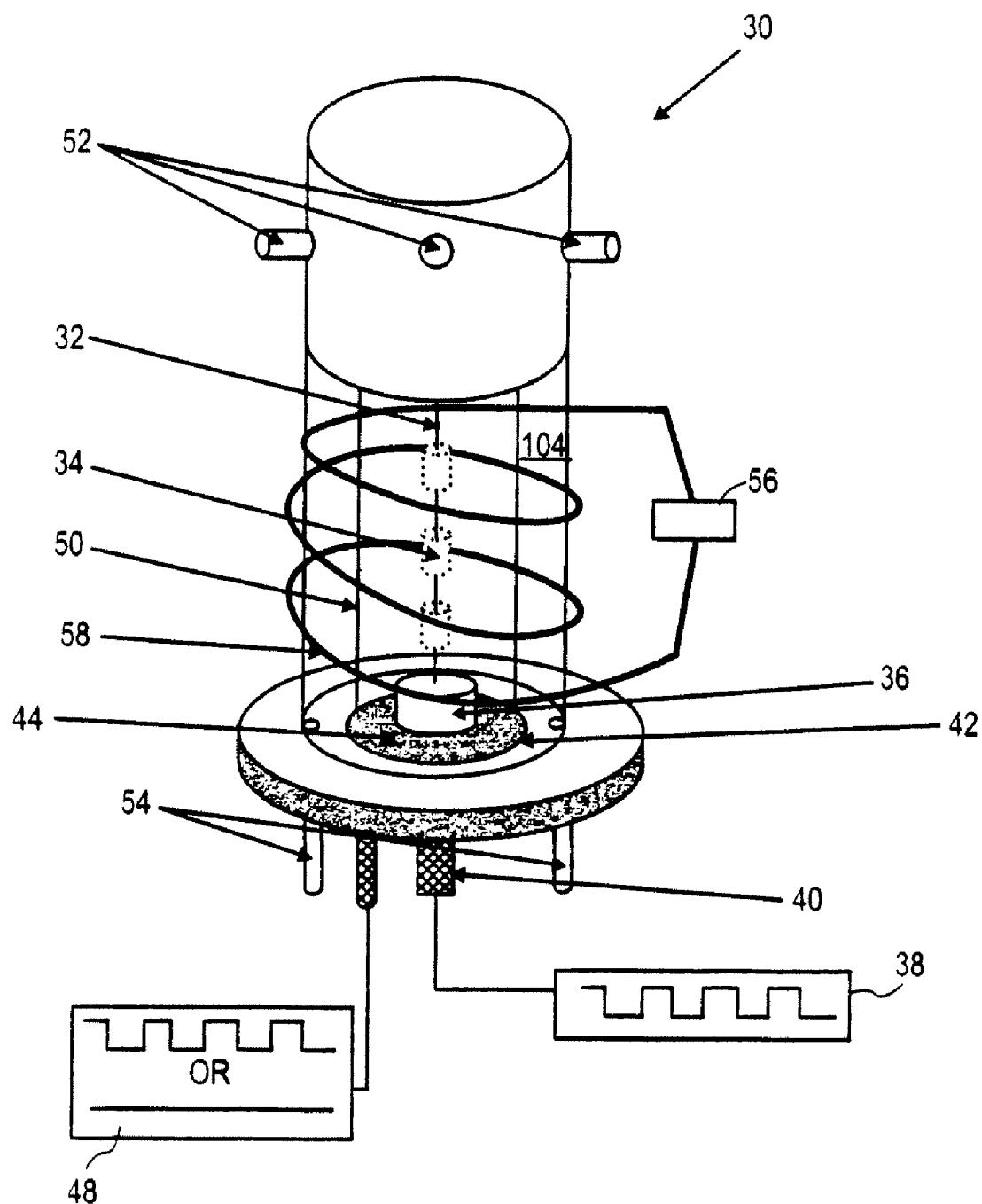
FIG. 10 illustrates an exemplary plasma chamber that can be used to practice the present invention.

Additionally, an apparatus for accomplishing the method of the present invention includes a plasma-generating assembly. The plasma-generating assembly can be, for example, a radio frequency source and antenna, a microwave source, or any other suitable element known to one of ordinary skill in the art. By way of example, FIG. 10 illustrates a radio frequency source 56, such as that manufactured by Dressler of Germany, and an antenna 58. In one such embodiment, antenna 58 can be a radio-frequency conducting filament that is wrapped about chamber 30 in a helical or corkscrew-like fashion.

While particular embodiments of the present invention have been shown and described, it will be obvious to those skilled in the art that changes and modification can be made without departing from this invention it its broader aspects and, therefore the appended claims are to encompass within their scope all such changes and modifications as fall within the true spirit and scope of this invention.

It is illustrated that the present invention enables coating of the SODm onto the surface of a pacemaker lead. However, it should be appreciated that the methods and the SODm coating described above can be applied to many other medical devices without deviating from the scope of the present invention. The method and the SODm coating described above are especially useful for coating SODm onto hard to coat materials (e.g., silicon rubber, fluoro polymer, polyethylene, and polypropylene) that are used to make many medical devices.

What is claimed is:

1. A medical device comprising:
   a substrate;
   a plasma polymerized functionality layer on at least a portion of the substrate, the plasma polymerized functionality layer having a first plurality of functional groups wherein the first plurality of functional groups is present in an amount to facilitate about 30 µg/mL density of a superoxide dismutase mimic agent bonded thereto; and
   the superoxide dismutase mimic agent bonded to the functionality layer, the superoxide dismutase mimic agent having a second plurality of functional groups complementary to the first plurality of functional groups.

2. The medical device of claim 1 wherein the first plurality of functional groups is selected from the group consisting of carboxylate, amine, and sulfate.

3. The medical device of claim 1 wherein the first plurality of functional groups comprise amine functional groups, the second plurality of functional groups also comprise amine functional groups, and a plurality of crosslinkers bonds the first plurality of functional groups and the second plurality of functional groups.

4. The medical device of claim 3 wherein the plurality of crosslinkers comprises at least one of a homobifunctional N-hydroxysuccinimide ester, disulfosuccinimidyl suberate, di succinimidyl suberate, bis(sulfosuccinimidyl)suberate, a bis imidoester, dimethyl pimelimidate, dimethyl suberimidate, dimethyl adipimidate, and dimethyl 3,3-dithiobispropionimidate.

5. The medical device of claim 1 wherein the first plurality of functional groups comprises carboxylate functional groups, the second plurality of functional groups comprise amine functional groups wherein the carboxylate functional groups bond to the amine functional groups.

6. The medical device of claim 1 further comprising a silicone layer coated on the substrate.

7. The medical device of claim 1 wherein the substrate is formed at least in part of a polymeric material selected from the group consisting of a fluoropolymer, polytetrafluoroethylene, expanded polytetrafluoroethylene, polyolefin, high density polyethylene, polyimide, polyetherether ketone, polyether urethane, polyurethane, polycarbonate urethane, siliconized urethane, and silicone rubber.

8. The medical device as in claim 1 wherein the polymerized functionality layer comprises a film having a thickness of about 25 nm to about 250 nm.

9. The medical device of claim 1 further comprising an electrically conductive electrophysiology lead implantable in a patient's heart having a component formed at least in part of the substrate.

10. The medical device of claim 1 further comprising a pacemaker lead implantable in a patient's heart having a component formed at least in part of the substrate.

11. The medical device of claim 1 further comprising an electrical signal generator and an electrically conductive electrophysiology lead implantable in a patient's heart having a component formed at least in part of the substrate.

12. The medical device of claim 1 wherein the first plurality of functional groups comprises one of carboxylate functional groups, the second plurality of functional groups comprise amine functional groups and polyethylene glycol functional groups, and the amine functional groups and the polyethylene glycol functional groups bond to the carboxylate functional groups.

* * * * *